(12) United States Patent
Lo et al.

(10) Patent No.: US 7,511,815 B2
(45) Date of Patent: Mar. 31, 2009

(54) DEVICE AND METHOD FOR MEASURING OPTICAL PARAMETERS OF LIQUID CRYSTAL DISPLAY

(75) Inventors: Ko-Chiang Lo, Taipei (TW); Jung-Chan Tsai, Taipei (TW)

(73) Assignee: Arima Display Corporation, Taipei (TW)

( * ) Notice: Subject to any disclaimer, the term of this patent is extended or adjusted under 35 U.S.C. 154(b) by 155 days.

(21) Appl. No.: 11/748,777

(22) Filed: May 15, 2007

(65) Prior Publication Data
US 2008/0285014 A1    Nov. 20, 2008

(51) Int. Cl.
*G01J 4/00* (2006.01)
(52) U.S. Cl. ........................................ 356/364; 356/327
(58) Field of Classification Search ................ 356/364, 356/327, 73
See application file for complete search history.

(56) References Cited

U.S. PATENT DOCUMENTS

2007/0153163 A1*  7/2007  Ito ............................... 349/96
2007/0206131 A1*  9/2007  Kondoh et al. ................ 349/96

* cited by examiner

*Primary Examiner*—Kara E Geisel
*Assistant Examiner*—Abdullahi Nur
(74) *Attorney, Agent, or Firm*—Volpe and Koenig, P.C.

(57) ABSTRACT

A device for measuring an optical property of a liquid crystal display is provided. The device has a light source providing a light, a first polarizer pervious to the light, a second polarizer pervious to the light, a detector receiving the light, and a calculating module. The first polarizer and the second polarizer are mounted between the light source and the detector, a first transmittance spectrum is obtained while the liquid crystal display is mounted between the first polarizer and the second polarizer, and a second transmittance spectrum is obtained while the liquid crystal display is mounted between the detector and the first and second polarizers.

20 Claims, 9 Drawing Sheets

Fig. 9

DEVICE AND METHOD FOR MEASURING OPTICAL PARAMETERS OF LIQUID CRYSTAL DISPLAY

FIELD OF THE INVENTION

The present invention relates to a device and a method for measuring an optical parameter of a liquid crystal display. In particular, the present invention relates to a device and a method for measuring the optical parameters including the twist angle of the liquid crystal, the alignment angle of emergence, the alignment angle of incidence, the viewing angle and the phase shifting values (Δnds) of the various wavelengths for a liquid crystal display.

BACKGROUND OF THE INVENTION

There are three main methods for measuring the optical properties of a liquid crystal, such as TN LCD, STN LCD and TN TFT LCD, in the prior arts. (1) The LCD to be detected is mounted between two polarizers each having an absorption-axis angle of 45°, and then a maximum absorption wavelength is obtained by a spectrophotometer or the device like that. Then, the phase shifting value (Δnd) of the liquid crystal display could be obtained from a predetermined equation relating to the maximum absorption wavelength and the Δnd, where the maximum absorption wavelength has a positive correlation with the Δnd. There are some disadvantages in this mentioned method. (a) It is unable to obtain the twist angle of the liquid crystal, i.e. the twist angle is necessary to be a known parameter. (b) It is unable to obtain the respective Δnds for various wavelengths. (c) Since the manufacturing process and the material of the LCD are the determinants of the correlation between the maximum absorption value and the Δnd, it is necessary to find out the respective correlations therebetween. (2) Based on the various twist angles of the liquid crystal, the LCD to be detected is mounted between two polarizers having the specific absorption angles, and then a maximum absorption wavelength is obtained by a spectrophotometer or the device like that. After that, the Δnd of the liquid crystal display could be obtained from a predetermined equation relating to the maximum absorption wavelength and the phase shifting value, where the maximum absorption wavelength has a positive correlation with the Δnd. There are some disadvantages in this mentioned method. (a) It is unable to obtain the twist angle of the liquid crystal i.e. the twist angle is necessary to be a known parameter. (b) It is unable to obtain the respective Δnds for various wavelengths. (c) Since the Δnd is obtained from the predetermined equation, there always exists an error therein. (3) The LCD to be tested is mounted between two polarizers, and a spectrophotometer or the device like that is applied. The absorption angles of the two polarizers are modified by try and error until the transmittance of the maximum absorption wavelength is the closest to zero and the maximum absorption wavelength would not change while rotating the panel. After that, it is able to obtain the twist angle of the crystal liquid, the Δnds after calculations, and then the correlation between the Δnds and the various wavelengths. The disadvantage for this method is the time waste during the try and error process.

As mentioned above, a device and a method for measuring an optical parameter of a liquid crystal display without the disadvantages of the prior arts are desires.

SUMMARY OF THE INVENTION

In accordance with an aspect of the present invention, a device for measuring an optical property of a liquid crystal display is provided. The device has a light source providing a light, a first polarizer pervious to the light, a second polarizer pervious to the light, a detector receiving the light, and a calculating module. The first polarizer and the second polarizer are mounted between the light source and the detector, a first transmittance spectrum is obtained while the liquid crystal display is mounted between the first polarizer and the second polarizer, and a second transmittance spectrum is obtained while the liquid crystal display is mounted between the detector and the first and second polarizers.

Preferably, the first transmittance spectrum is obtained from the detector and the calculating module.

Preferably, the second transmittance spectrum is obtained from the detector and the calculating module.

Preferably, a third transmittance spectrum is obtained by dividing the first transmittance spectrum by the second transmittance spectrum.

Preferably, the third transmittance spectrum is a specific transmittance spectrum (T) obtained from an equation as follows:

$$T=\frac{1}{2}[\cos^2(\alpha-\beta)-\sin^2 X \sin 2\beta \sin 2\alpha+(\emptyset/2X)\sin 2X \sin 2(\alpha-\beta)-\emptyset^2(\sin^2 X/X^2)\cos 2\beta \cos 2\alpha]$$

wherein,

α=an transmission-axis angle at the entrance side–an alignment angle at the entrance site;

β=a transmission-axis angle at the exit side–an alignment angle at the exit side;

Ø=a twist angle of the liquid crystal;

$X=[\emptyset^2+(2\pi\Delta nd/\lambda)^2/4]^{1/2}$;

λ a wavelength of an incident light; and $\Delta nd=a+b/\lambda^2+c/\lambda^4$, wherein a, b and c are variables.

Preferably, the calculating module performs a calculation of the equation.

Preferably, the optical property of the liquid crystal display is one selected from the group consisting of an incident alignment angle, an emergent alignment angle, a viewing angle and a phase shift value.

Preferably, the liquid crystal display is one selected from the group consisting of TN LCD, STN LCD, and TN TFT LCD.

In addition, a method for measuring an optical property of a liquid crystal display is provided. The method includes steps of (a) obtaining a first transmittance of the liquid crystal display while the liquid crystal display is mounted between a first polarizer and a second polarizer, (b) obtaining a second transmittance of the liquid crystal display while the liquid crystal display is mounted between a detector and the first and second polarizers, (c) dividing the first transmittance spectrum by the second transmittance spectrum to obtain a third transmittance spectrum serving as a transmittance spectrum (T) in the following equation, $$T=\frac{1}{2}[\cos^2(\alpha-\beta)-\sin^2 X \sin 2\beta \sin 2\alpha+(\emptyset/2X)\sin 2X \sin 2(\alpha-\beta)-\emptyset^2(\sin^2 X/X^2)\cos 2\beta \cos 2\alpha]$$

wherein,

α=an transmission-axis angle at the entrance side–an alignment angle at the entrance site;

β=a transmission-axis angle at the exit side–an alignment angle at the exit side;

Ø=a twist angle of the liquid crystal;

$X=[\emptyset^2+(2\pi\Delta nd/\lambda)^2/4]^{1/2}$;

λ=a wavelength of an incident light; and $\Delta nd=a+b/\lambda^2+c/\lambda^4$, wherein a, b and c are variables, and (d) obtaining the optical property of the liquid crystal display by the equation after a regression analysis.

Preferably, the first transmittance of the liquid crystal display is obtained via the detector.

Preferably, the second transmittance of the liquid crystal display is obtained via the detector.

Preferably, the optical property of the liquid crystal display is one selected from the group consisting of an incident alignment angle, an emergent alignment angle, a viewing angle and a phase shift value.

Preferably, the liquid crystal display is one selected from the group consisting of TN LCD, STN LCD, and TN TFT LCD.

Preferably, the regression analysis is performed by a software.

In another respect of the present application, a device for measuring an optical property of a liquid crystal display is provided. The device includes a light source providing a light, a first site for setting the liquid crystal display, a second site for setting the liquid crystal display, and a detector receiving the light. The first site and the second site are mounted between the light source and the detector, a first transmittance spectrum is obtained while the liquid crystal display is mounted on the first site, and a second transmittance spectrum is obtained while the liquid crystal display is mounted on the second site.

Preferably the device further has a polarizer.

Preferably, the device further includes a calculating module.

Preferably, a third transmittance spectrum is obtained by dividing the first transmittance spectrum by the second transmittance spectrum.

Preferably, the third transmittance spectrum is a specific transmittance spectrum (T) obtained from an equation as follows:

$$T=\frac{1}{2}[\cos^2(\alpha-\beta)-\sin^2 X \sin 2\beta \sin 2\alpha + (\emptyset/2X)\sin 2X \sin 2(\alpha-\beta) - \emptyset^2(\sin^2 X/X^2)\cos 2\beta \cos 2\alpha]$$

wherein, $\alpha$=an transmission-axis angle at the entrance side−an alignment angle at the entrance site;

$\beta$=a transmission-axis angle at the exit side−an alignment angle at the exit side;

$\emptyset$=a twist angle of the liquid crystal;

$X=[\emptyset^2+(2\pi\Delta nd/\lambda)^2/4]^{1/2}$;

$\lambda$=a wavelength of an incident light; and $\Delta nd=a+b/\lambda^2+c/\lambda^4$, wherein a, b and c are variables.

In accordance with another respect of the present application, a method for measuring an optical property of a liquid crystal display is provided. The method includes steps of (a) obtaining a first transmittance of the liquid crystal display while the liquid crystal display is mounted on a first site, (b) obtaining a second transmittance of the liquid crystal display while the liquid crystal display is mounted on a second site, (c) dividing the first transmittance spectrum by the second transmittance spectrum to obtain a third transmittance spectrum serving as a transmittance spectrum (T) in the following equation;

$$T=\frac{1}{2}[\cos^2(\alpha-\beta)-\sin^2 X \sin 2\beta \sin 2\alpha + (\emptyset/2X)\sin 2X \sin 2(\alpha-\beta) - \emptyset^2(\sin^2 X/X^2)\cos 2\beta \cos 2\alpha]$$

wherein, $\alpha$=an transmission-axis angle at the entrance side−an alignment angle at the entrance site;

$\beta$=a transmission-axis angle at the exit side−an alignment angle at the exit side;

$\emptyset$=a twist angle of the liquid crystal;

$X=[\emptyset^2+(2\pi\Delta nd/\lambda)^2/4]^{1/2}$;

$\lambda$=a wavelength of an incident light; and $\Delta nd=a+b/\lambda^2+c/\lambda^4$, wherein a, b and c are variables, and (d) obtaining the optical property of the liquid crystal display by the equation after a regression analysis.

The above contents and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Based on Pochi Yeh & Claire Gu edited "*Optics of Liwuid Crystal Displays*", John Wiley & Sons, Inc., 1999, and the Jones vector, it is practicable to obtain the transmittance spectrum of the crystal liquid display from the following equation (I), which is called Yeh & Gu equation hereinafter.

$$T=\frac{1}{2}[\cos^2(\alpha-\beta)-\sin^2 X \sin 2\beta \sin 2\alpha + (\emptyset/2X)\sin 2X \sin 2(\alpha-\beta) - \emptyset^2(\sin^2 X/X^2)\cos 2\beta \cos 2\alpha] \quad (I)$$

wherein, $\alpha$=an transmission-axis angle at the entrance side−an alignment angle at the entrance site;

$\beta$=a transmission-axis angle at the exit side−an alignment angle at the exit side;

$\emptyset$=a twist angle of the liquid crystal;

$X=[\emptyset^2+(2\pi\Delta nd/\lambda)^2/4]^{1/2}$;

$\lambda$=a wavelength of an incident light; and $\Delta nd=a+b/\lambda^2+c/\lambda^4$, wherein a, b and c are variables.

The correlation between the respective $\Delta nd$s under various wavelengths is obtained from Cauchy function. After a regression analysis between the theoretical transmittance spectrum curve of the variables $\emptyset$, a, b, c, $\alpha$, $\beta$ and the really detected transmittance spectrum curve, it is able to obtain the mentioned six variables. And then, it is practicable to obtain the optical properties of the detected liquid crystal display. While the "alignment direction" of the panel and the twist angle of the liquid crystal display are known, it is able to know the mentioned variables $\emptyset$, $\alpha$, and $\beta$ therefrom. And then, only the variables a, b and c are performed in the regression analysis.

Figure 1:
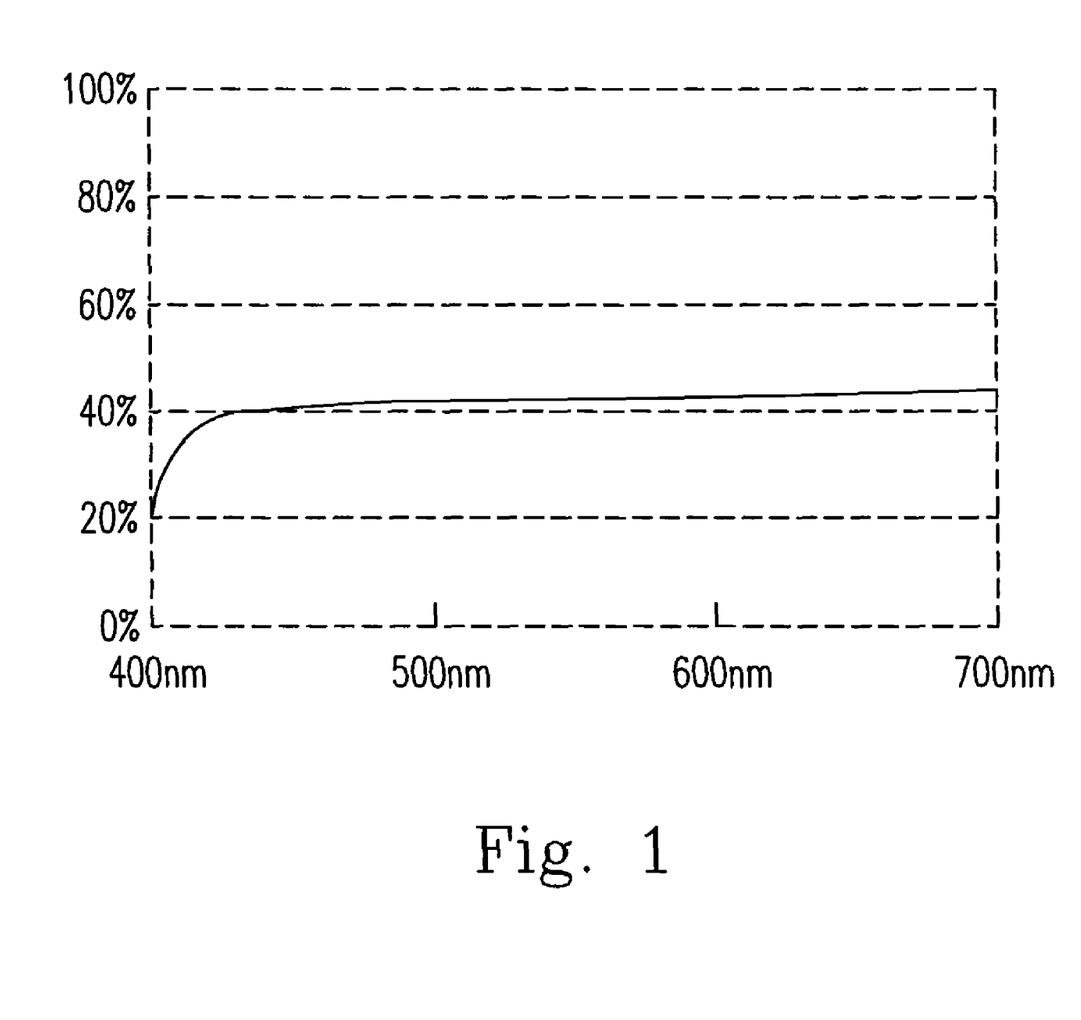
FIG. 1 shows the transmittance spectrums curve while only a single polarizer is used.
Figure 2:
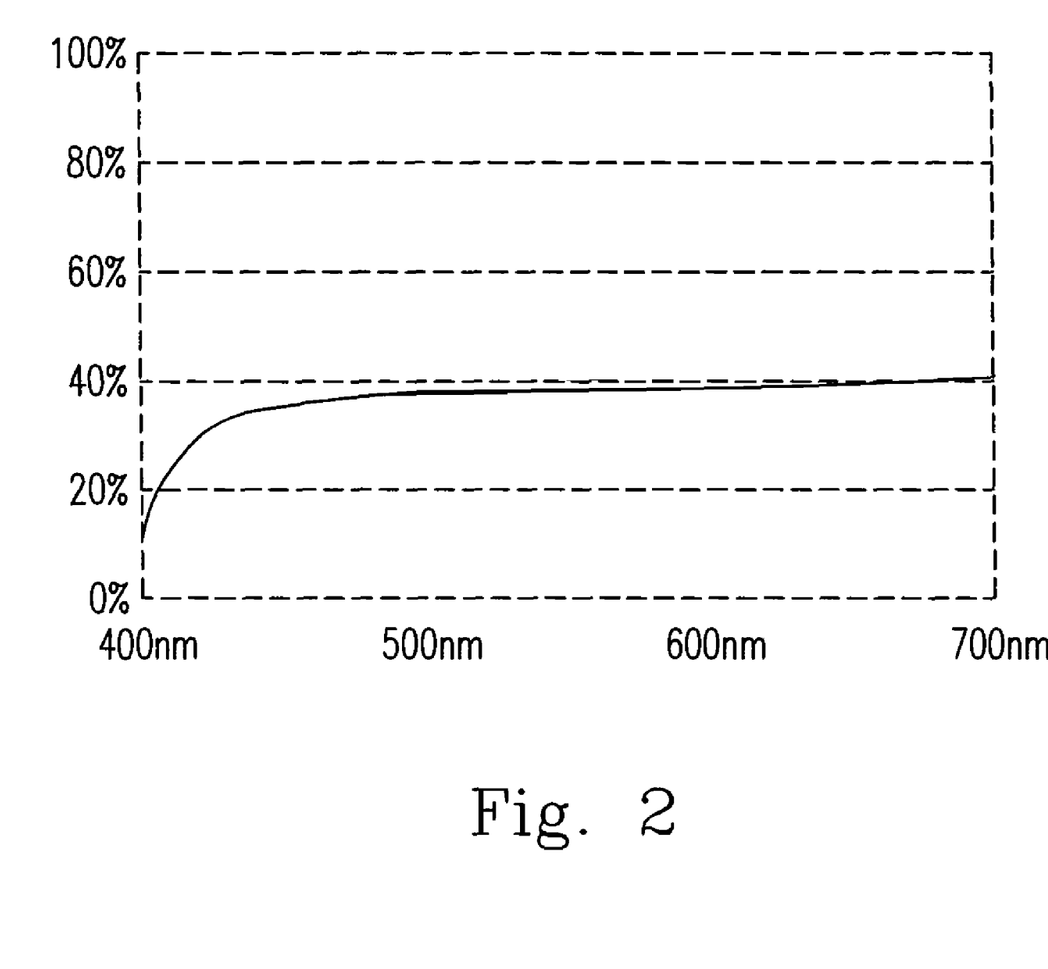
FIG. 2 shows the transmittance spectrum curve while two polarizers are paralleled with each other.

In order to practice the above method, it is necessary to assume the polarizing elements are ideal and having the following properties: (a) the transmittance rate of the light is 50% while transmitting through these polarizing elements, (b) the transmittance rate of the light is 50% while these polarizing elements are parallel with each other, and (c) the transmittance rate of the light is 0% while these polarizing elements are perpendicular to each other. Nevertheless, actually, the polarizing elements have their own transmittance spectrums, such as FIGS. 1 and 2. FIG. 1 shows the transmittance spectrums curve while only a single polarizer is used, and FIG. 2 shows the transmittance spectrum curve while two polarizers are paralleled with each other.

Figure 3:
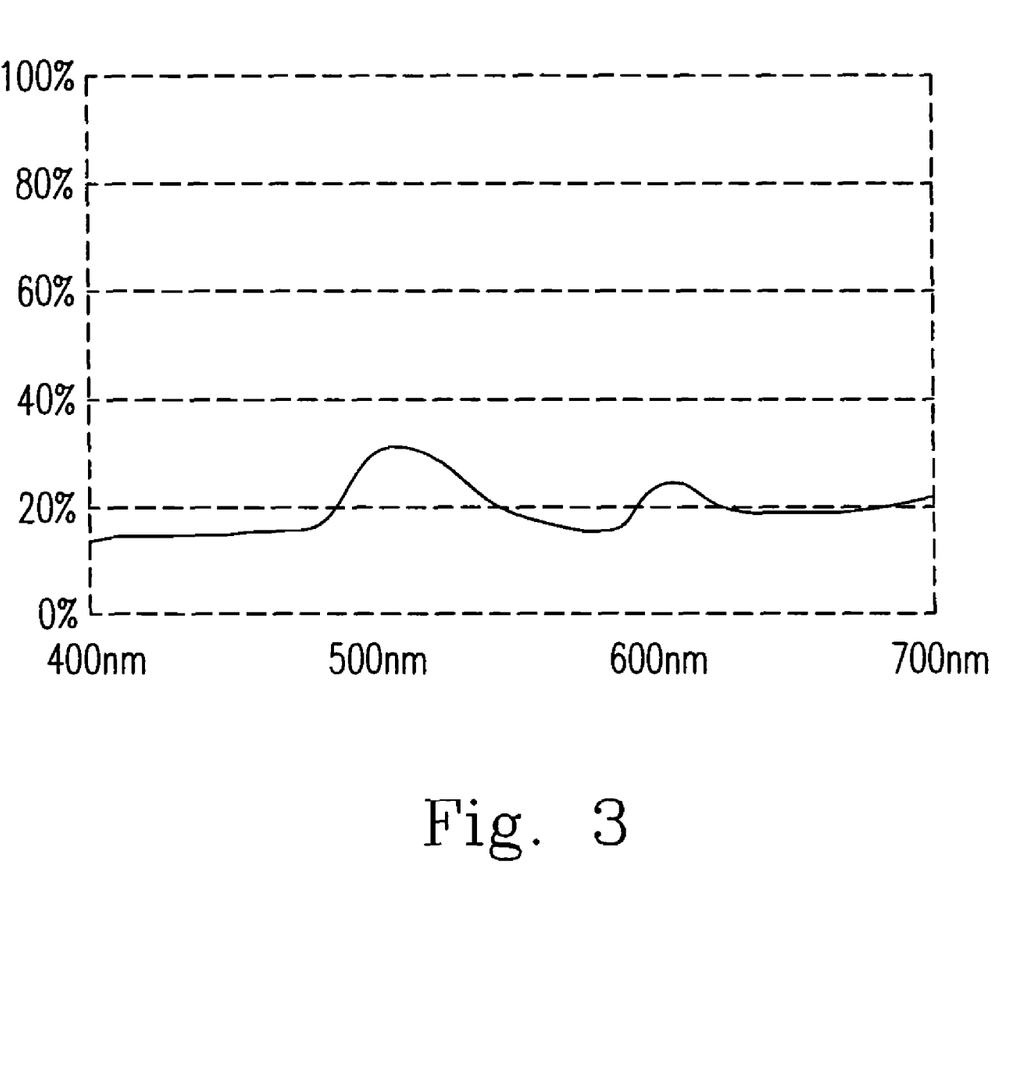
FIG. 3 is a transmittance spectrum curve of a color STN liquid crystal display without polarizer.
Figure 4:
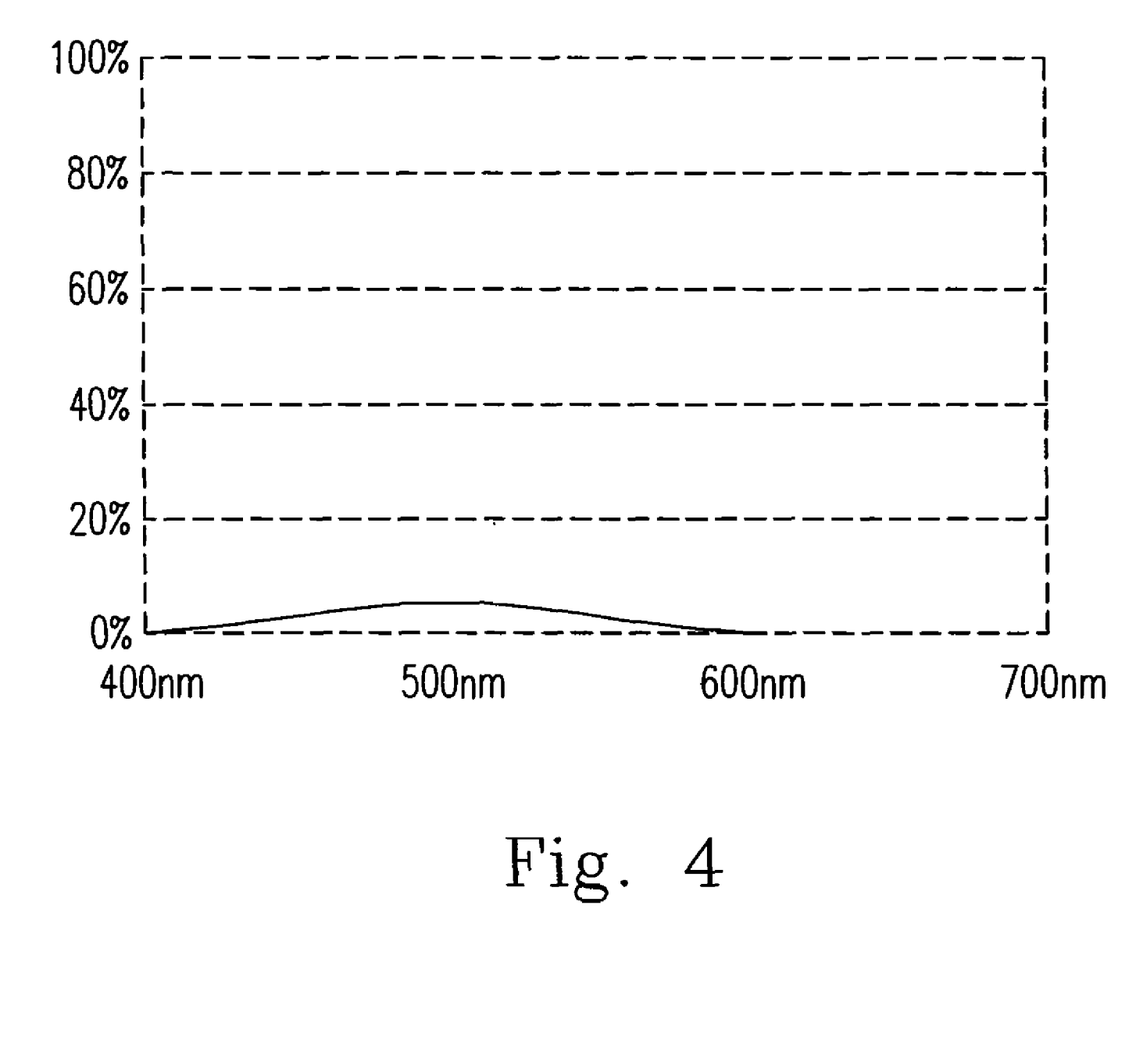
FIG. 4 shows the transmittance spectrum curve while the color STN liquid crystal display is mounted between two polarizers.

If it is assumed that the transmittances of the materials for the respective layers in the liquid crystal display are all 100%, and then the transmittance spectrum of the liquid crystal display are only correlative with the $\varnothing$, $\alpha$, $\beta$ and $\Delta$nd. Actually, however, the respective layers, such as the glass layer, the liquid crystal layer and the alignment film of the liquid crystal display have their own transmittance spectrums, so that the liquid crystal display has its transmittance spectrum, such as FIG. 3. FIG. 3 is a transmittance spectrum curve of a color STN liquid crystal display without polarizer. Furthermore, while the color STN liquid crystal display is mounted between two polarizers, the transmittance spectrum curve is shown in FIG. 4.

Figure 5:
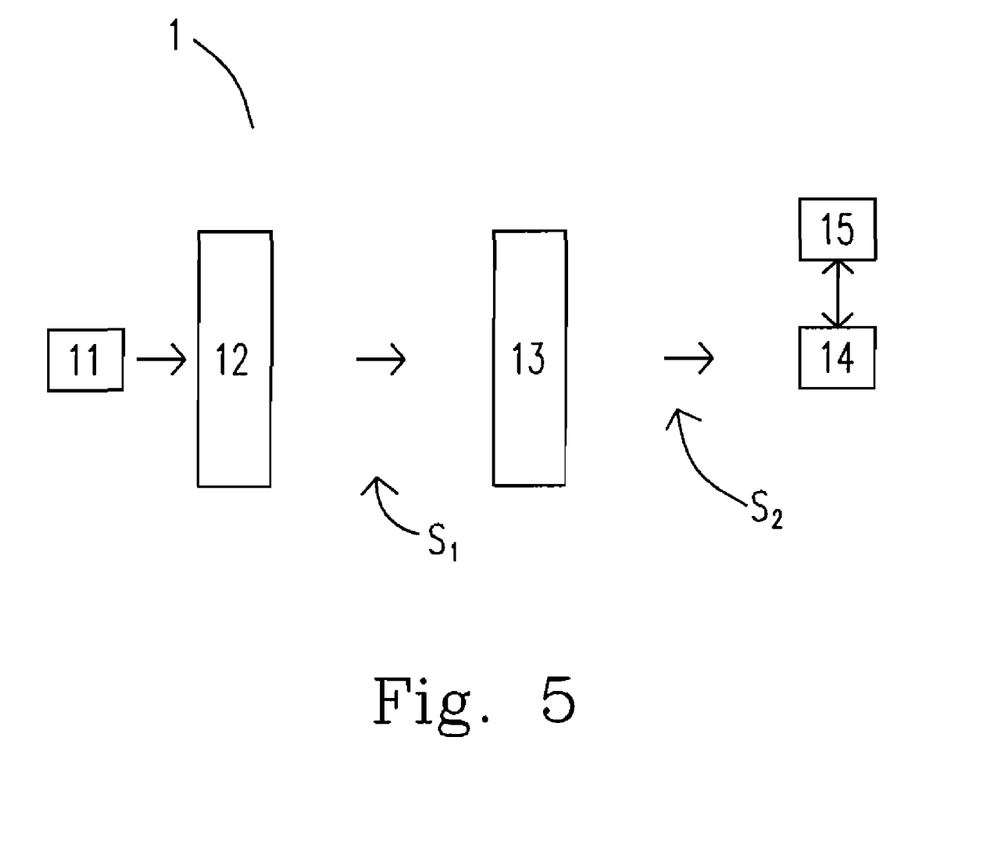
FIG. 5 shows a device for measuring the optical properties of a liquid crystal display according to a preferred embodiment of the present application.

In order to solve the mentioned drawbacks, a device and a method are further provided. Please refer to FIG. 5, which shows a device for measuring the optical properties of a liquid crystal display according to a preferred embodiment of the present application. As shown in FIG. 5, the device 1 includes a light source 11, a first polarizer 12, a second polarizer 13, a detector 14 and a calculating module 15. A first site S1 for setting a display to be tested (not shown) is between the first polarizer 12 and the second polarizer 13, and a second site S2 for setting a display to be tested (not shown) is between the second polarizer 13 and the detector 14. In this embodiment, the first polarizer 12 and the second polarizer 13 are the polarizers made by TAIWAN NITTO OPTICAL CO., LTD, Type TEG1465DU. In addition, the device 1 in this embodiment could be built as a spectrophotometer.

Figure 6:
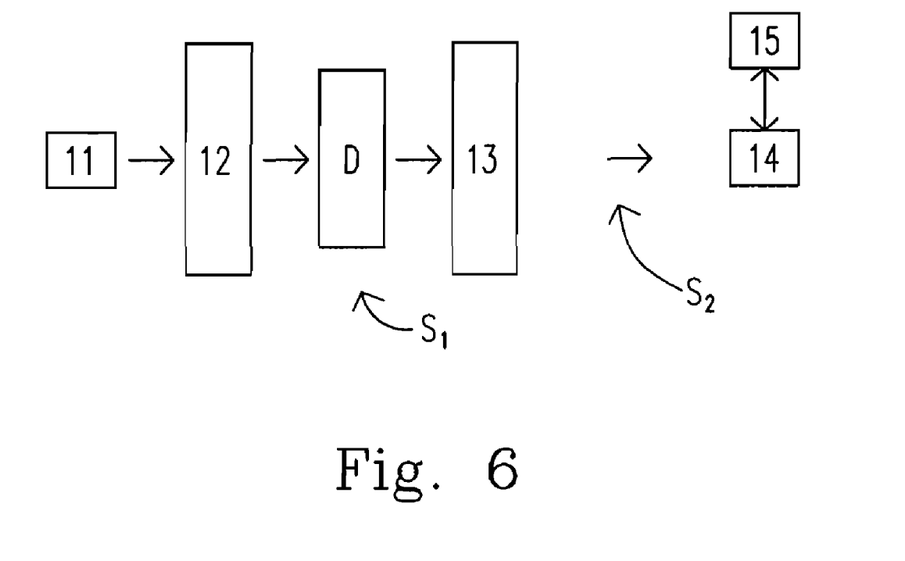
FIG. 6 is a diagram showing a display is testing in the device of FIG. 5.

Please refer to FIG. 6, which is a diagram showing a display is testing in the device of FIG. 5. As shown in FIG. 6, the liquid crystal display D is mounted in the first site S1. The first polarizer 12 and the second polarizer 13 have the same absorption-axis angle. A first transmittance spectrum named T1 (not shown in FIG. 6) is obtained after the analysis of detector 14 and the calculation of calculating module 15 while the liauid display D is mounted in the first site S1. It is to be noted that the calculating module 15 might be set within the detector 14 in some embodiments.

Please refer to FIG. 6, which is a diagram showing a display is testing in the device of FIG. 5. As shown in FIG. 6, the liquid crystal display D is mounted in the first site S1. In this embodiment, the first polarizer 12 and the second polarizer 13 have the same absorption-axis angle. While a light transmitted from the light source 11 transmits through the first polarizer 11, the liquid crystal display D and the second polarizer 13 in turn and is received by the detector 14, a first transmittance spectrum named T1 (not shown in FIG. 6) could be obtained after the analysis of detector 14 and the calculation of calculating module 15.

Figure 7:
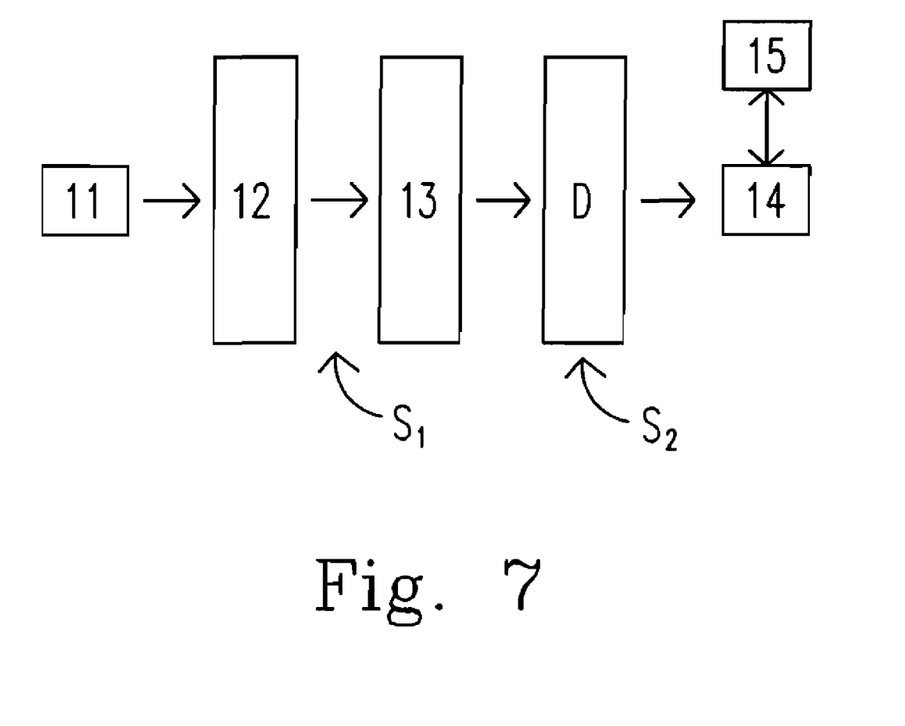
FIG. 7 is a diagram showing a display is testing in the device of FIG. 5.

Please refer to FIG. 7, which is a diagram showing a display is testing in the device of FIG. 5. As shown in FIG. 7, the liquid crystal display D is mounted in the second site S2. In this embodiment, the first polarizer 12 and the second polarizer 13 have the same absorption-axis angle. While a light transmitted from the light source 11 transmits through the first polarizer 11, the second polarizer 13 and the liquid crystal display D in turn and is received by the detector 14, a second transmittance spectrum named T2 (not shown in FIG. 7) could be obtained after the analysis of detector 14 and the calculation of calculating module 15.

A third transmittance spectrum T3 is obtained via dividing T1 by T2. Then, the third transmittance spectrum T3 is considered as transmittance spectrum T in the mentioned equation (I). Since the angles of the first and second polarizers 12 and 13 could be modified, various T3s could be obtained under various angles of the first and second polarizers 12 and 13. After a regression of the various T3s with a value-analysis program, such as Excel 2003 from Microsoft, it would be possible to find out the variables variables $\varnothing$, a, b, c, $\alpha$, $\beta$ in the mentioned equation (I). While the variables $\varnothing$, a, b, c, $\alpha$, $\beta$ are known, the $\Delta$nds under various wavelengths and other properties of the tested liquid crystal display could be obtained accordingly.

Table 1 shows a calculating result of a tested liquid crystal display while two polarizers each having a transmittance-angle of 45° are used in the present application.

TABLE 1 a calculating result of a tested liquid crystal display

| $\varnothing$ | a | B | c | $\alpha$ |
|---|---|---|---|---|
| 239.6° | 697.45 | $1.9397 \times 10^7$ | $3.2267 \times 10^{12}$ | −105.2° |

Figure 8:
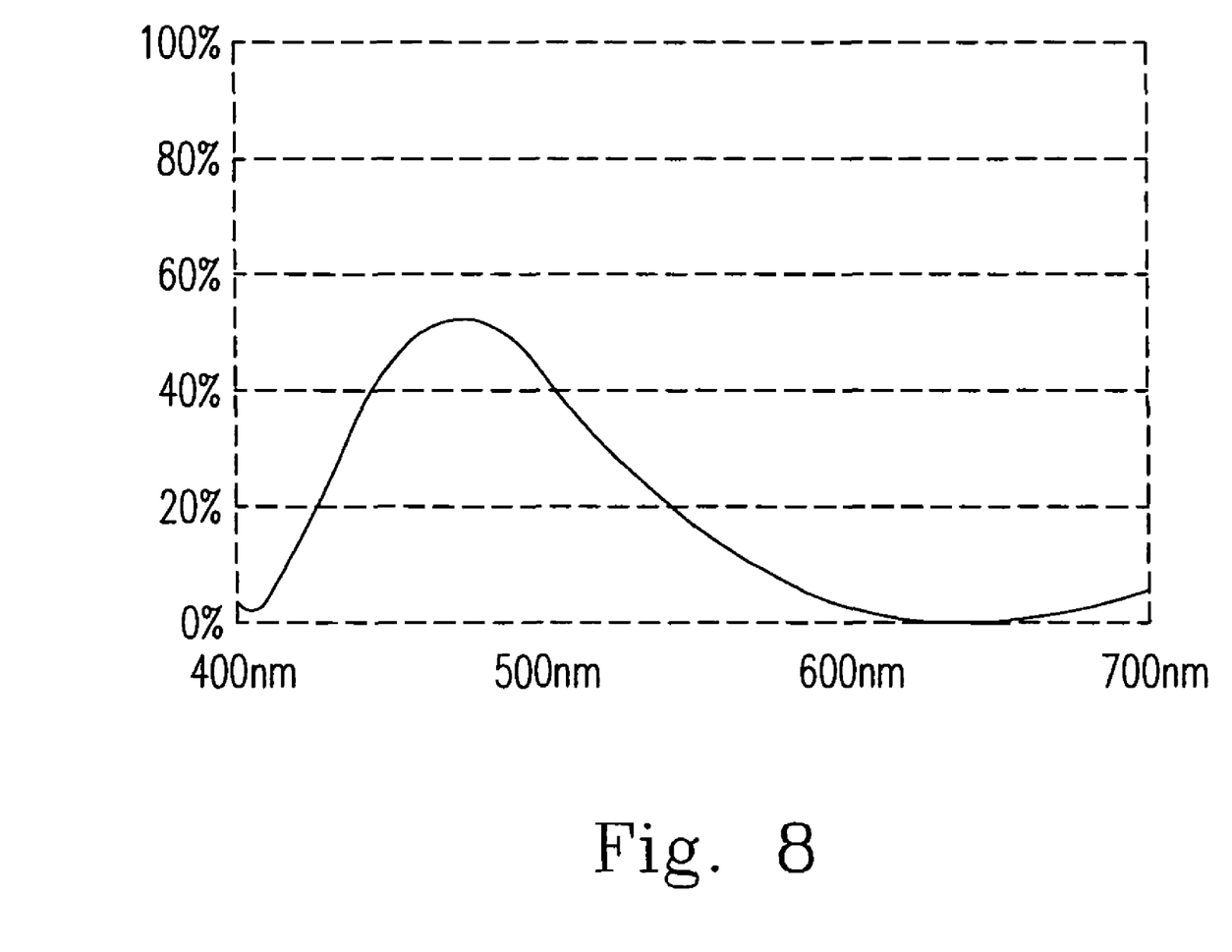
FIG. 8 is diagram showing the transmittance spectrum of a color STN liquid crystal display mounted between the first and second polarizers.
Figure 9:
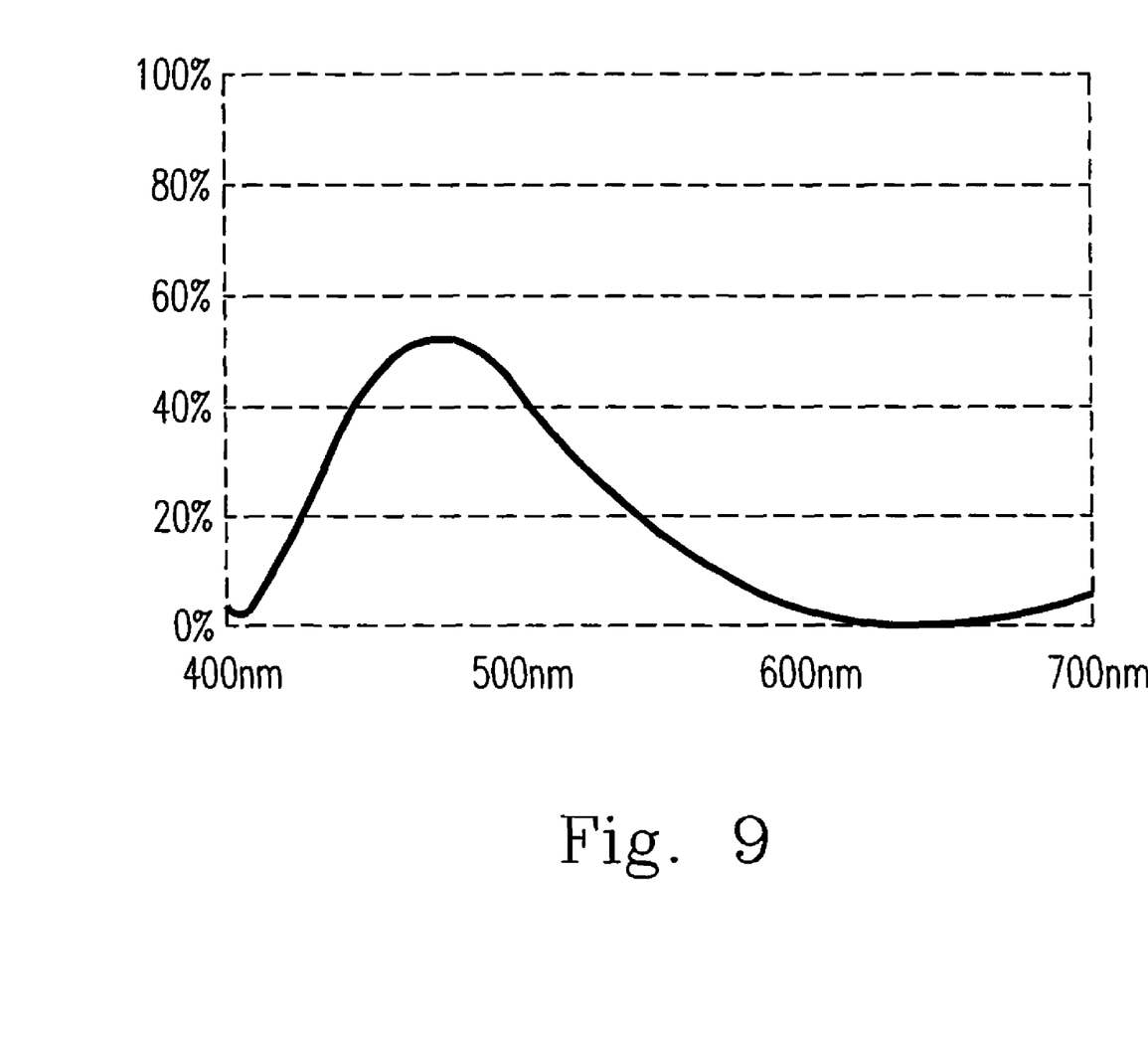
FIG. 9 shows the transmittance spectrum after a regression analysis of the color STN liquid crystal display.

Please refer to FIGS. 8 and 9, FIG. 8 is diagram showing the transmittance spectrum of a color STN liquid crystal display mounted between the first and second polarizers, and FIG. 9 shows the transmittance spectrum after a regression analysis of the color STN liquid crystal display.

Since the operation of the present application is simple, the material cost is low, the calculation programs are easily-obtained and it is easy and rapid to obtain the twist angle of the liquid, the alignment angle at the entrance site, the alignment angle at the exit site, the viewing angle and the $\Delta$nds under various wavelengths, the present application is novel, non-obvious and has industry value.

While the invention has been described in terms of what is presently considered to be the most practical and preferred embodiment, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A device for measuring an optical property of a liquid crystal display, comprising:
   a light source providing a light;
   a first polarizer pervious to the light;
   a second polarizer pervious to the light;
   a detector receiving the light; and
   a calculating module,
   wherein the first polarizer and the second polarizer are mounted between the light source and the detector, a first transmittance spectrum is obtained while the liquid crystal display is mounted between the first polarizer and the second polarizer, and a second transmittance spectrum is obtained while the liquid crystal display is mounted between the detector and the first and second polarizers.

2. A device as claimed in claim 1, wherein the first transmittance spectrum is obtained from the detector and the calculating module.

3. A device as claimed in claim 1, wherein the second transmittance spectrum is obtained from the detector and the calculating module.

4. A device as claimed in claim 1, wherein a third transmittance spectrum is obtained by dividing the first transmittance spectrum by the second transmittance spectrum.

5. A device as claimed in claim 4, wherein the third transmittance spectrum is a specific transmittance spectrum (T) obtained from an equation as follows:

$$T=\tfrac{1}{2}[\cos^2(\alpha-\beta)-\sin^2 X\sin 2\beta \sin 2\alpha+(\varnothing/2X)\sin 2X \sin 2(\alpha-\beta)-\varnothing^2(\sin^2 X/X^2)\cos 2\beta \cos 2\alpha]$$

wherein,
α=an transmission-axis angle at the entrance side–an alignment angle at the entrance site;
β=a transmission-axis angle at the exit side–an alignment angle at the exit side;
Ø=a twist angle of the liquid crystal;
$X=[\varnothing^2+(2\pi\Delta nd/\lambda)^2/4]^{1/2}$;
λ=a wavelength of an incident light; and
$\Delta nd=a+b/\lambda^2+c/\lambda^4$, wherein a, b and c are variables.

6. A device as claimed in claim 5, wherein the calculating module performs a calculation of the equation.

7. A device as claimed in claim 1, wherein the optical property of the liquid crystal display is one selected from the group consisting of an incident alignment angle, an emergent alignment angle, a viewing angle and a phase shift value.

8. A device as claimed in claim 1, wherein the liquid crystal display is one selected from the group consisting of TN LCD, STN LCD, and TN TFT LCD.

9. A method for measuring an optical property of a liquid crystal display, comprising steps of:
(a) obtaining a first transmittance of the liquid crystal display while the liquid crystal display is mounted between a first polarizer and a second polarizer;
(b) obtaining a second transmittance of the liquid crystal display while the liquid crystal display is mounted between a detector and the first and second polarizers;
(c) dividing the first transmittance spectrum by the second transmittance spectrum to obtain a third transmittance spectrum serving as a transmittance spectrum (T) in the following equation;

$$T=\tfrac{1}{2}[\cos^2(\alpha-\beta)-\sin^2 X\sin 2\beta \sin 2\alpha+(\varnothing/2X)\sin 2X \sin 2(\alpha-\beta)-\varnothing^2(\sin^2 X/X^2)\cos 2\beta \cos 2\alpha]$$

wherein,
α=an transmission-axis angle at the entrance side–an alignment angle at the entrance site;
β=a transmission-axis angle at the exit side–an alignment angle at the exit side;
Ø=a twist angle of the liquid crystal;
$X=[\varnothing^2+(2\pi\Delta nd/\lambda)^2/4]^{1/2}$;
λ=a wavelength of an incident light; and
$\Delta nd=a+b/\lambda^2+c/\lambda^4$, wherein a, b and c are variables, and
(d) obtaining the optical property of the liquid crystal display by the equation after a regression analysis.

10. A method as claimed in claim 9, wherein the first transmittance of the liquid crystal display is obtained via the detector.

11. A method as claimed in claim 9, wherein the second transmittance of the liquid crystal display is obtained via the detector.

12. A method as claimed in claim 9, wherein the optical property of the liquid crystal display is one selected from the group consisting of an incident alignment angle, an emergent alignment angle, a viewing angle and a phase shift value.

13. A method as claimed in claim 9, wherein the liquid crystal display is one selected from the group consisting of TN LCD, STN LCD, and TN TFT LCD.

14. A method as claimed in claim 9, wherein the regression analysis is performed by a software.

15. A device for measuring an optical property of a liquid crystal display, comprising:
a light source providing a light;
a first site for setting the liquid crystal display;
a second site for setting the liquid crystal display; and
a detector receiving the light;
wherein the first site and the second site are mounted between the light source and the detector, a first transmittance spectrum is obtained while the liquid crystal display is mounted on the first site, and a second transmittance spectrum is obtained while the liquid crystal display is mounted on the second site.

16. A device as claimed in claim 15, further comprising a polarizer.

17. A device as claimed in claim 15, further comprising a calculating module.

18. A device as claimed in claim 15, wherein a third transmittance spectrum is obtained by dividing the first transmittance spectrum by the second transmittance spectrum.

19. A device as claimed in claim 18, wherein the third transmittance spectrum is a specific transmittance spectrum (T) obtained from an equation as follows:

$$T=\tfrac{1}{2}[\cos^2(\alpha-\beta)-\sin^2 X\sin 2\beta \sin 2\alpha+(\varnothing/2X)\sin 2X \sin 2(\alpha-\beta)-\varnothing^2(\sin^2 X/X^2)\cos 2\beta \cos 2\alpha]$$

wherein,
α=an transmission-axis angle at the entrance side–an alignment angle at the entrance site;
β=a transmission-axis angle at the exit side–an alignment angle at the exit side;
Ø=a twist angle of the liquid crystal;
$X=[\varnothing^2+(2\pi\Delta nd/\lambda)^2/4]^{1/2}$;
λ=a wavelength of an incident light; and
$\Delta nd=a+b/\lambda^2+c/\lambda^4$, wherein a, b and c are variables.

20. A method for measuring an optical property of a liquid crystal display, comprising steps of:
(a) obtaining a first transmittance of the liquid crystal display while the liquid crystal display is mounted on a first site;
(b) obtaining a second transmittance of the liquid crystal display while the liquid crystal display is mounted on a second site;
(c) dividing the first transmittance spectrum by the second transmittance spectrum to obtain a third transmittance spectrum serving as a transmittance spectrum (T) in the following equation;

$$T=\tfrac{1}{2}[\cos^2(\alpha-\beta)-\sin^2 X\sin 2\beta \sin 2\alpha+(\varnothing/2X)\sin 2X \sin 2(\alpha-\beta)-\varnothing^2(\sin^2 X/X^2)\cos 2\beta \cos 2\alpha]$$

wherein,
α=an transmission-axis angle at the entrance side–an alignment angle at the entrance site;
β=a transmission-axis angle at the exit side–an alignment angle at the exit side;
Ø=a twist angle of the liquid crystal;
$X=[\varnothing^2+(2\pi\Delta nd/\lambda)^2/4]^{1/2}$;
λ=a wavelength of an incident light; and
$\Delta nd=a+b/\lambda^2+c/\lambda^4$, wherein a, b and c are variables, and
(d) obtaining the optical property of the liquid crystal display by the equation after a regression analysis.

* * * * *